(12) United States Patent
Schraga

(10) Patent No.: US 8,118,825 B2
(45) Date of Patent: Feb. 21, 2012

(54) LANCET DEVICE

(76) Inventor: Steven Schraga, Surfside, FL (US)

( * ) Notice: Subject to any disclaimer, the term of this patent is extended or adjusted under 35 U.S.C. 154(b) by 674 days.

(21) Appl. No.: 10/716,385

(22) Filed: Nov. 18, 2003

(65) Prior Publication Data

US 2004/0147948 A1 Jul. 29, 2004

Related U.S. Application Data

(63) Continuation-in-part of application No. 10/134,995, filed on Apr. 29, 2002, now abandoned.

(51) Int. Cl.
*A61B 17/32* (2006.01)

(52) U.S. Cl. ............................................. 606/182

(58) Field of Classification Search .......... 606/181–183; 600/583; 604/164.08, 164.12, 192–193, 604/197–198, 162, 253
See application file for complete search history.

(56) References Cited

U.S. PATENT DOCUMENTS

| | | | |
|---|---|---|---|
| 55,775 A | 6/1866 | Klee | |
| 2,711,738 A | 6/1955 | Kelly et al. | |
| 3,358,689 A | 12/1967 | Higgins | |
| 3,483,810 A | 12/1969 | Peters et al. | |
| 3,760,809 A | 9/1973 | Campbell, Jr. | |
| 3,906,626 A | 9/1975 | Riuli | |
| 4,139,011 A | 2/1979 | Benoit et al. | |
| 4,338,871 A | 7/1982 | van der Lely | |
| 4,373,526 A | 2/1983 | Kling | |
| 4,414,975 A | 11/1983 | Ryder et al. | |
| 4,445,896 A | 5/1984 | Gianturco | |
| 4,449,529 A | 5/1984 | Burns et al. | |
| 4,469,110 A | 9/1984 | Slama | |
| 4,517,978 A | 5/1985 | Levin et al. | |
| 4,535,769 A | 8/1985 | Burns | |
| 4,539,988 A | 9/1985 | Shirley et al. | |
| 4,573,976 A | 3/1986 | Sampson et al. | |
| 4,610,620 A | 9/1986 | Gray | |
| 4,655,750 A | 4/1987 | Vaillancourt | |
| 4,665,959 A | 5/1987 | Takagi | |
| 4,715,374 A | 12/1987 | Maggio | |
| 4,735,202 A | 4/1988 | Williams | |
| 4,735,203 A | 4/1988 | Ryder et al. | |
| 4,752,290 A | 6/1988 | Schramm | |
| 4,758,230 A | 7/1988 | Rycroft | |
| 4,758,231 A | 7/1988 | Haber et al. | |
| 4,794,926 A | 1/1989 | Munsch et al. | |
| 4,817,603 A * | 4/1989 | Turner et al. | 606/182 |
| 4,823,806 A | 4/1989 | Bajada | |

(Continued)

FOREIGN PATENT DOCUMENTS

CA  2 261 852 A1  8/1999

(Continued)

*Primary Examiner* — Ryan Severson
(74) *Attorney, Agent, or Firm* — Malloy & Malloy, P.L.

(57) ABSTRACT

A lancet device including a housing with an at least partially open interior, a cocking seat coupled with the housing and structured to define an open interior therewith, a lancet with a piercing tip moveably disposed within the open interior, and a biasing assembly engaging the lancet. The cocking seat is structured to engage the lancet and retain the lancet against a force of the biasing assembly so as to maintain a potential energy of the biasing assembly. A release element is provided to at least partially disengage the lancet from the cocking seat such that the potential energy of the biasing assembly moves the lancet relative to the cocking seat and drives the piercing tip of the lancet at least temporarily into a piercing orientation.

1 Claim, 3 Drawing Sheets

U.S. PATENT DOCUMENTS

| | | | |
|---|---|---|---|
| 4,841,985 A | 6/1989 | Wanamaker | |
| 4,863,436 A | 9/1989 | Glick | |
| 4,869,249 A | 9/1989 | Crossman et al. | |
| 4,889,117 A | 12/1989 | Stevens | |
| 4,892,097 A | 1/1990 | Ranalletta et al. | |
| 4,895,147 A | 1/1990 | Bodicky et al. | |
| 4,897,083 A | 1/1990 | Martell | |
| 4,907,600 A | 3/1990 | Spencer | |
| 4,908,023 A | 3/1990 | Yuen | |
| 4,944,736 A | 7/1990 | Holtz | |
| 4,969,883 A | 11/1990 | Gilbert et al. | |
| 4,983,178 A | 1/1991 | Schnell | |
| 4,990,154 A | 2/1991 | Brown et al. | |
| 4,994,045 A | 2/1991 | Ranford | |
| 4,994,068 A | 2/1991 | Hufnagle | |
| 5,024,660 A | 6/1991 | McNaughton | |
| 5,026,388 A | 6/1991 | Ingalz | |
| 5,057,079 A | 10/1991 | Tiemann et al. | |
| 5,070,885 A | 12/1991 | Bonaldo | |
| 5,074,872 A | 12/1991 | Brown et al. | |
| 5,086,780 A | 2/1992 | Schmitt | |
| 5,088,996 A | 2/1992 | Kopfer et al. | |
| 5,116,351 A | 5/1992 | Frassetti | |
| 5,125,921 A | 6/1992 | Duschek | |
| 5,147,326 A | 9/1992 | Talonn et al. | |
| 5,147,375 A | 9/1992 | Sullivan et al. | |
| 5,160,326 A | 11/1992 | Talonn et al. | |
| 5,181,609 A | 1/1993 | Spielmann et al. | |
| 5,188,620 A | 2/1993 | Jepson et al. | |
| 5,201,716 A | 4/1993 | Richard | |
| 5,207,696 A | 5/1993 | Matwijcow | |
| 5,207,699 A | 5/1993 | Coe | |
| 5,219,333 A | 6/1993 | Sagstetter et al. | |
| 5,222,945 A | 6/1993 | Basnight | |
| 5,224,950 A | 7/1993 | Prywes | |
| 5,230,707 A | 7/1993 | Laderoute | |
| 5,241,969 A | 9/1993 | Carson et al. | |
| 5,247,972 A | 9/1993 | Tetreault | |
| 5,250,026 A | 10/1993 | Ehrlich et al. | |
| 5,250,063 A | 10/1993 | Abidin et al. | |
| 5,269,799 A | 12/1993 | Danielsson | |
| 5,279,581 A | 1/1994 | Firth et al. | |
| 5,297,599 A | 3/1994 | Bucheli | |
| 5,304,136 A | 4/1994 | Erskine et al. | |
| 5,304,192 A | 4/1994 | Crouse | |
| 5,304,193 A | 4/1994 | Zhadanov | |
| 5,312,347 A | 5/1994 | Osborne et al. | |
| 5,312,354 A | 5/1994 | Allen et al. | |
| 5,312,365 A | 5/1994 | Firth et al. | |
| 5,318,583 A | 6/1994 | Rabenau et al. | |
| 5,318,584 A | 6/1994 | Lange et al. | |
| 5,330,492 A | 7/1994 | Haugen | |
| 5,336,199 A | 8/1994 | Castillo et al. | |
| 5,346,480 A | 9/1994 | Hess et al. | |
| 5,350,392 A | 9/1994 | Purcell et al. | |
| 5,356,406 A | 10/1994 | Schraga | |
| 5,356,420 A * | 10/1994 | Czernecki et al. | 606/182 |
| 5,361,902 A | 11/1994 | Abidin et al. | |
| 5,395,388 A | 3/1995 | Schraga | |
| 5,417,662 A | 5/1995 | Hjertman et al. | |
| 5,423,847 A | 6/1995 | Strong et al. | |
| 5,439,473 A * | 8/1995 | Jorgensen | 606/182 |
| 5,454,828 A | 10/1995 | Schraga | |
| 5,462,535 A | 10/1995 | Bonnichsen et al. | |
| 5,464,418 A | 11/1995 | Schraga | |
| 5,468,233 A | 11/1995 | Schraga | |
| 5,469,964 A | 11/1995 | Bailey | |
| 5,487,748 A | 1/1996 | Marshall et al. | |
| 5,496,340 A | 3/1996 | Abidin et al. | |
| 5,501,672 A | 3/1996 | Firth et al. | |
| 5,514,152 A | 5/1996 | Smith | |
| 5,518,004 A | 5/1996 | Schraga | |
| 5,527,334 A | 6/1996 | Kanner et al. | |
| 5,531,713 A | 7/1996 | Mastronardi et al. | |
| D376,203 S | 12/1996 | Schraga | |
| 5,584,846 A | 12/1996 | Mawhirt et al. | |
| 5,599,323 A | 2/1997 | Bonnichsen et al. | |
| 5,628,764 A | 5/1997 | Schraga | |
| 5,628,765 A * | 5/1997 | Morita | 606/182 |
| 5,643,306 A | 7/1997 | Schraga | |
| 5,697,916 A | 12/1997 | Schraga | |
| 5,706,942 A | 1/1998 | Vila et al. | |
| 5,707,384 A | 1/1998 | Kim | |
| 5,709,700 A | 1/1998 | Hirota | |
| 5,730,753 A | 3/1998 | Morita | |
| 5,735,823 A | 4/1998 | Berger | |
| 5,738,665 A | 4/1998 | Caizza et al. | |
| 5,741,288 A | 4/1998 | Rife | |
| 5,746,761 A | 5/1998 | Turchin | |
| 5,755,733 A | 5/1998 | Morita | |
| 5,772,636 A | 6/1998 | Brimhall et al. | |
| 5,792,122 A | 8/1998 | Brimhall et al. | |
| 5,797,940 A | 8/1998 | Mawhirt et al. | |
| 5,797,942 A | 8/1998 | Schraga | |
| 5,836,920 A | 11/1998 | Robertson | |
| 5,868,771 A | 2/1999 | Herbert et al. | |
| 5,871,494 A | 2/1999 | Simons et al. | |
| 5,873,856 A | 2/1999 | Hjertman et al. | |
| 5,891,103 A | 4/1999 | Burns | |
| 5,908,434 A | 6/1999 | Schraga | |
| 5,916,230 A | 6/1999 | Brenneman et al. | |
| 5,947,924 A | 9/1999 | Liprie | |
| 5,947,934 A | 9/1999 | Hansen et al. | |
| 5,951,530 A | 9/1999 | Steengaard et al. | |
| 5,951,582 A | 9/1999 | Thorne et al. | |
| 5,954,738 A | 9/1999 | LeVaughn et al. | |
| 5,968,021 A | 10/1999 | Ejlersen | |
| 5,971,966 A | 10/1999 | Lav | |
| 5,980,491 A | 11/1999 | Hansen | |
| 5,984,906 A | 11/1999 | Bonnichsen et al. | |
| 6,015,397 A | 1/2000 | Elson et al. | |
| 6,022,366 A | 2/2000 | Schraga | |
| 6,050,977 A | 4/2000 | Adams | |
| 6,056,765 A | 5/2000 | Bajaj et al. | |
| 6,074,372 A | 6/2000 | Hansen | |
| 6,077,253 A | 6/2000 | Cosme | |
| 6,106,537 A | 8/2000 | Crossman et al. | |
| 6,110,149 A | 8/2000 | Klitgaard et al. | |
| 6,136,013 A | 10/2000 | Marshall et al. | |
| 6,149,608 A | 11/2000 | Marshall et al. | |
| 6,156,051 A | 12/2000 | Schraga | |
| 6,168,606 B1 | 1/2001 | Levin et al. | |
| 6,190,398 B1 | 2/2001 | Schraga | |
| 6,213,977 B1 | 4/2001 | Hjertman et al. | |
| 6,216,868 B1 | 4/2001 | Rastegar et al. | |
| 6,228,100 B1 | 5/2001 | Schraga | |
| 6,248,120 B1 * | 6/2001 | Wyszogrodzki | 606/182 |
| 6,258,112 B1 | 7/2001 | Schraga | |
| 6,299,626 B1 | 10/2001 | Viranyi | |
| 6,302,869 B1 | 10/2001 | Klitgaard | |
| 6,316,114 B1 | 11/2001 | Comer et al. | |
| 6,322,574 B1 | 11/2001 | Lloyd et al. | |
| 6,322,575 B1 | 11/2001 | Schraga | |
| 6,346,114 B1 | 2/2002 | Schraga | |
| 6,358,265 B1 | 3/2002 | Thorne, Jr. et al. | |
| 6,432,120 B1 | 8/2002 | Teo | |
| 6,514,270 B1 | 2/2003 | Schraga | |
| 6,530,937 B1 | 3/2003 | Schraga | |
| 6,719,771 B1 | 4/2004 | Crossman | |
| 6,764,496 B2 | 7/2004 | Schraga | |
| 6,852,119 B1 | 2/2005 | Abulhaj et al. | |
| 6,887,253 B2 | 5/2005 | Schraga | |
| 6,918,918 B1 | 7/2005 | Schraga | |
| 6,949,111 B2 | 9/2005 | Schraga | |
| 6,958,072 B2 | 10/2005 | Schraga | |
| 7,105,006 B2 | 9/2006 | Shraga | |
| 7,575,583 B1 | 8/2009 | Schraga | |
| 7,621,931 B2 | 11/2009 | Shraga | |
| 7,678,126 B2 | 3/2010 | Schraga | |
| 2002/0004649 A1 * | 1/2002 | Jansen et al. | 604/198 |
| 2004/0102802 A1 | 5/2004 | Marshall | |
| 2005/0070945 A1 | 3/2005 | Schraga | |
| 2005/0245955 A1 | 11/2005 | Schraga | |
| 2006/0058828 A1 | 3/2006 | Shi | |
| 2006/0079920 A1 | 4/2006 | Schraga | |

| | | | |
|---|---|---|---|
| 2006/0178686 A1 | 8/2006 | Schraga | |
| 2006/0184189 A1 | 8/2006 | Olson et al. | |
| 2010/0305598 A1 | 12/2010 | Schraga | |

FOREIGN PATENT DOCUMENTS

| | | |
|---|---|---|
| CA | 2 450 711 A1 | 6/2003 |
| CN | 2621601 | 6/2004 |
| CN | 03220517.1 | 6/2004 |
| CN | 02815771.0 | 10/2004 |
| CN | 00817325.7 | 6/2005 |
| CN | 1846612 A | 10/2006 |
| DE | 203 13 528 U1 | 1/2004 |
| EP | 0 115 388 A1 | 8/1984 |
| EP | 0 595 148 A1 | 5/1994 |
| EP | 0 633 004 A1 | 1/1995 |
| EP | 0 668 049 A1 | 8/1995 |
| EP | 0 894 471 A2 | 3/1999 |
| EP | 0 940 121 A2 | 9/1999 |
| EP | 0 958 783 A1 | 11/1999 |
| EP | 1 233 706 A0 | 8/2002 |
| EP | 1 501 428 A0 | 2/2005 |
| FR | 1.126.718 | 11/1956 |
| GB | 2 052 992 A | 2/1981 |
| HK | 1055234 B | 2/2006 |
| JP | 2003-512883 A | 4/2003 |
| JP | 2005-511191 A | 4/2005 |
| JP | 2006-218301 A | 8/2006 |
| WO | WO 91/00215 | 1/1991 |
| WO | WO 98/55034 | 12/1998 |
| WO | WO 00/78203 A2 | 12/2000 |
| WO | WO 03/049624 A1 | 6/2003 |
| WO | WO 03/092512 A1 | 11/2003 |

* cited by examiner

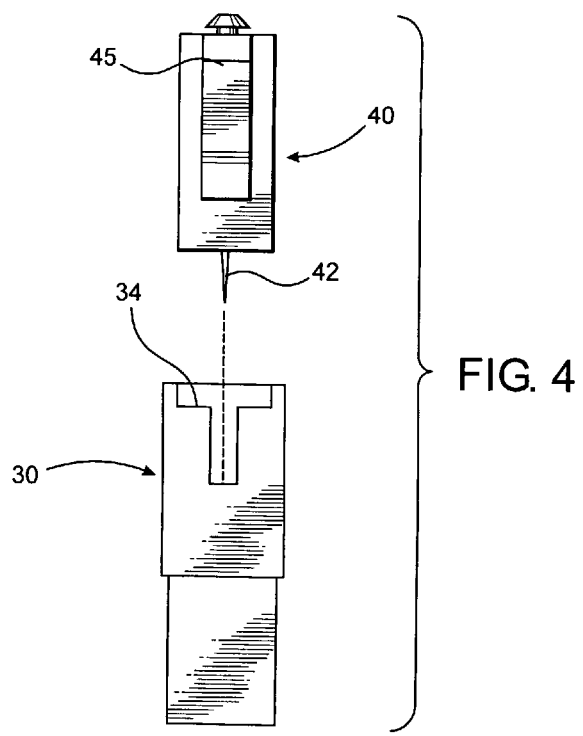
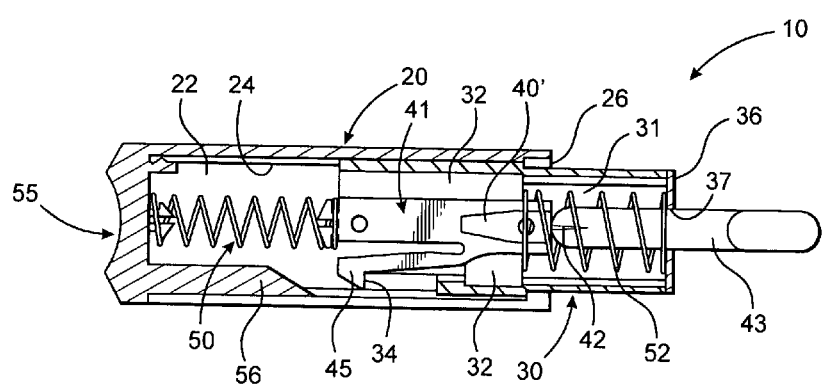

LANCET DEVICE

CLAIM OF PRIORITY

The present application is a continuation-in-part application of previously filed, now application having Ser. No. 10/134,995, filed on Apr. 29, 2002 now abandoned.

BACKGROUND OF THE INVENTION

1. Field of the Invention

The present invention relates to a lancet device preferably configured to provide a single use, and in all embodiments configured to substantially shield and protect a piercing tip thereof before and after use, while providing for accurate and effective piercing engagement of a patient's skin when appropriate. Furthermore, the present lancet device does not require complex and/or difficult to manipulate cocking and is structured such that the device is rendered in-operative after a single use.

2. Description of the Related Art

Lancets are commonly utilized instruments which are employed both in hospitals and other medical facilities, as well as by private individuals, such as diabetics, in order to prick or pierce a patient's skin, typically on a finger of a patient, thereby leading to the generation of a blood sample which can be collected for testing. Because of the wide spread use of such lancets, there are a variety of lancet devices which are available for utilization by patients and/or practitioners in a variety of different circumstances.

For example, a typical lancet may merely include a housing with a sharp piercing tip that is pushed into the patient's skin. More commonly, however, lancet devices, which house a piercing tip and/or a lancet, have been developed which effectively encase and fire the lancet into the patient's skin, thereby eliminating the need for the person taking the sample to actually push the lancet tip into the skin.

Within the various types of specialized lancet devices, one variety is typically configured for multiple and/or repeated uses, while another category is particularly configured for single use, after which the entire device is disposed of. Looking in particular to the single use, disposable lancet devices, such devices typically include a housing which contains and directs or drives a piercing tip into the patient's skin, and which is disposed of along with the used lancet. Naturally, so as to make such disposable devices cost effective for frequent use, such devices tend to be rather simplistic in nature providing only a sufficient mechanism for firing, and not overly complicating the design so as to minimize that cost.

While existing single use devices are generally effective for achieving the piercing of the skin required for effective operation, such single use, disposable devices typically do not incorporate a large number of safety features to ensure the safe use and disposal of the device. For example, one primary area of safety which must be addressed with all lancet devices pertains to the purposeful and/or inadvertent reuse of a contaminated lancet. Unfortunately, most currently available single use lancet devices are configured such that after a use thereof has been achieved, it is possible for a patient to re-cock the device, thereby allowing for a subsequent, inappropriate use.

As a result, it would be highly beneficial to provide a single use lancet device which is substantially compact and disposable, can be manufactured in a substantially cost effective manner, and which nevertheless is substantially safe to utilize, affirmatively preventing re-use, once contaminated.

A further drawback associated with conventionally employed single use lancet devices is that they can often be difficult and/or complicated for elderly and/or impaired individuals to manipulate in order to achieve effective use. In particular, such existing devices often require a user to perform a number of different actions, including one to cock and thereby prepare the device for use, and another to actually fire the device. As can be appreciated, those procedures, even in the simplest form, can sometimes be complex and/or difficult to effectively achieve on a small compact device by certain individuals, and especially those individuals performing self testing who necessarily only have one hand to use to manipulate the device. Indeed, to avoid these complexities, some manufactures have turned to the use of pre-cocked and ready to use devices, however, this can often result in misfires and/or pre-fires of the lancet such that a certain of percentage of the lancet devices are not usable.

As a result, it would also be beneficial to provide a lancet device, which whether single use and/or multiple use, could be very simplistic and effective to employ, not requiring a series of often complex activities to be performed in order to prepare the lancet for use and in order to actually utilize the lancet. Still, however, such a device should not compromise safety in the prevention of inadvertent use and/or re-use in exchange for the simplistic use, but rather should effectively coordinate all such beneficial characteristics. It would also be beneficial such a device could be cost effectively manufactured so as to make it available and affordable to a large variety of users, including home users.

SUMMARY OF THE INVENTION

The present invention relates to a lancet device, and preferably a single use lancet device, utilized so as to effectively pierce a patient's skin and result in bleeding for subsequent sample collection. The lancet device of the present invention preferably includes a housing having an at least partially open interior. Furthermore, a lancet is movably disposed relative to the housing and includes a piercing tip which ultimately will penetrate the patient's skin. Similarly, a biasing assembly is interposed between the lancet and the housing. The biasing assembly engages the lancet and functions to urge the lancet into its piercing orientation, when appropriate.

The lancet device of the present invention also includes a cocking seat. The cocking seat is structured to engage the lancet and retain the lancet against the force of the biasing assembly so as to establish a potential energy of the biasing assembly. In the preferred embodiment, the user's finger and/or another body part which is to be pierced, engages the cocking seat and thereby pushes the cocking seat and the lancet until it ultimately engages a release assembly that extends into the housing. In alternate embodiments, the cocking seat is integrally or separately disposed relative to the housing to retain the lancet against the force of a biasing element until released by actuating a release assembly. The release assembly is structured to disengage the lancet from the cocking seat such that the potential energy of the biasing assembly drives the piercing tip of the lancet at least temporarily into its piercing orientation. As a result, in one illustrated embodiment, as the cocking seat moves the lancet, simultaneously cocking it and moving it into its engaging relation with the release element for effective actuation and firing thereof to pierce the skin of the patient, while in another embodiment, the lancet device is "pre-cocked".

These and other features and advantages of the present invention will become more clear when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which:

FIG. 4 is an exploded view of the lancet device and cocking seat of a preferred embodiment of the present invention;

FIG. 5 is a side cross-section view of still another embodiment of the lancet device of the present invention illustrating a re-usable configuration thereof.

Like reference numerals refer to like parts throughout the several views of the drawings.

DETAILED DESCRIPTION OF THE PREFERRED EMBODIMENT

Figure 1:
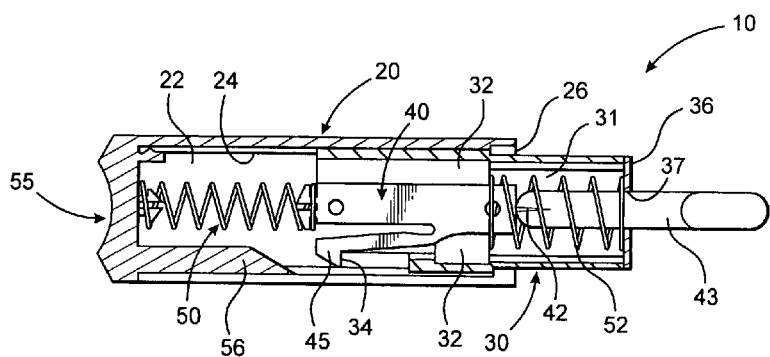
FIG. 1 is a side cross-sectional view of a preferred embodiment of the lancet device of the present invention in an unused orientation.

Shown throughout the Figures, the present invention is directed towards a lancet device, generally indicated as 10. In one embodiment of the present invention, as illustrated in FIGS. 1 through 3 and 6 the lancet device 10 is preferably a single use device such that after it is utilized for the first and only time it is configured so as to prevent subsequent use. Ultimately, however, as illustrated in FIG. 5, a re-usable configuration may be provided.

Looking specifically to the Figures, the lancet device of the present preferably includes a housing 20. The housing 20 includes an at least partially open interior 22 and can be made of any variety materials, but preferably will be formed of a molded plastic type material for ease of manufacture and minimization of cost. Also in the preferred embodiment, the housing 20 preferably includes an open end 26, which may represent a general front of the lancet device 10, and may include any variety of axial configurations, including a square, triangle, oval, circle, etc., although a generally elongated, longitudinal configuration as illustrated in the Figures is preferred in conjunction therewith.

The lancet device 10 further includes a lancet 40 movably disposed at least partially within the housing 20 and including a piercing tip 42. In the single use embodiment of FIGS. 1 through 3 and 6 the lancet 40 is a single integral unit as shown. Alternatively, as illustrated in the embodiment of FIG. 5, what is referred to as a lancet in the claims may include a lancet body 40' from which the piercing tip 42 extends, as well as a lancet receiving assembly 41, into which the lancet body 40' is disposed for movable retention. In such an embodiment, each time the lancet device 10 is to be re-used, a new lancet body 40' with piercing tip 42 is disposed within the lancet receiving assembly 41. In either embodiment, however, the lancet is movably disposed within the housing 20.

Figure 2:
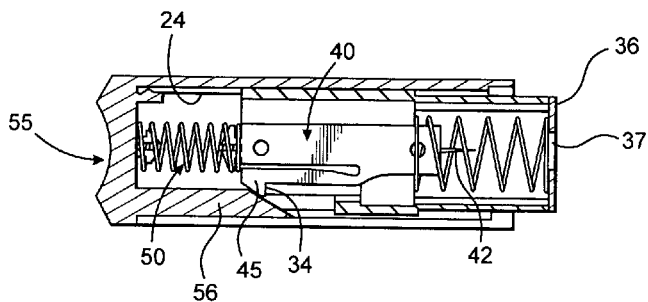
FIG. 2 is a side cross-section view of the embodiment of FIG. 1 in a substantially cocked and immanent to release orientation.

Preferably the lancet engages a biasing assembly also preferably disposed within the housing 20. In the illustrated preferred embodiments, the biasing assembly includes a biasing element 50 such as a metal or plastic spring. Preferably, the biasing element 50 is interposed between the lancet 40 and a rear end 55, 55' of the housing 20. The rear end 55, 55' may be unitary or separate from the housing 20. Moreover, positioned so as to engage the lancet 40 and retain it under the tension of the biasing assembly 50 is a cocking seat 30. In particular, the cocking seat 30 is structured to engage the lancet 40 and retain the lancet 40 against a force of the biasing assembly 50 so as to maintain a potential energy of the biasing assembly 50. In some illustrated embodiments, and as best seen in FIG. 2, the cocking seat 30 urges the lancet 40 towards the rear end of the lancet housing 20, thereby resulting in a compression of the biasing assembly 50 and an increase in the potential energy thereof. Further, so as to maintain effectively appropriate alignment of the lancet and the cocking seat 30 as they are moving relative to the housing 20, in the preferred embodiment, a guide track assembly 24, 32 may be provided between the cocking seat 30 and the housing 20.

Figure 6:
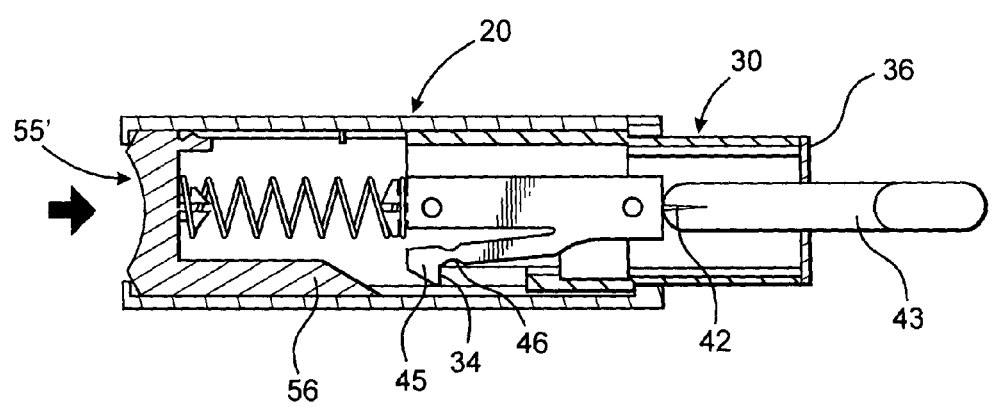
FIG. 6 is a side cross-section view of another embodiment of the lancet device of the present invention illustrating a fixed cocking seat.

In the preferred, illustrated embodiments, an engagement assembly 34, 45 is provided and preferably interposed between the cocking seat 30 and the lancet 40 so as to maintain moving engagement between the lancet 40 and the cocking seat 30 until they are disengaged, as will be described. In the illustrated embodiments, the engagement assembly includes an engagement element 45 that extends from lancet 40 into effectively retained, engaging relation with a retention lip 34 on the cocking seat 30. As a result, as the cocking seat 30 moves inward towards the rear end 55 of the housing 20, the effective engagement between the engagement element 45 and the retention lip 34 results in movement of the lancet 40 in unison with the cocking seat 30. In this regard, it is understood that a variety of different engagement assemblies, including one in which the engagement element extends from the cocking seat into engagement with a corresponding retention lip on the lancet, may also effectively be provided, the engagement assembly being configured so as to provide for effective substantially, although not necessarily completely, unitary movement between the lancet 40 and the cocking seat 30 until effective release thereby, as will be described. Further, in yet another embodiment, as seen in FIG. 6, the cocking seat may be pre-introduced into housing, or be integrally formed with or secured to the housing 20 such that the lancet 40 is effectively maintained under a tension of the biasing assembly until released by a moveable release assembly.

In particular, the present lancet device 10 further includes a release element 56. In the illustrated embodiments, the engagement element 45 of the engagement assembly preferably has a generally flexible and/or resilient characteristic relative to the lancet 40, and/or as will be described, includes a single use pivot 46. As a result, when the cocking seat 30 and therefore the lancet 40 are urged sufficiently into an interior 22 of housing 20, the release element 56 which also at least partially extends into an interior of the housing 20 when firing is desired, serves to engage the engagement element 45, and ultimately causes upward movement thereof for disengagement between the engagement element 45 and a retention lip 34. Moreover, this disengagement is achieved after a substantial amount of potential energy has been achieved in the biasing assembly 50. As a result, disengagement between the lancet 40 and the cocking seat 30 results in the lancet 40 moving relative to the cocking seat 30 under a force achieved by the potential energy stored in the biasing assembly 50. The guide track 32 may also serve to guide generally linear movement of the lancet 40 relative to the cocking seat 30, as the lancet 40 moves to the open interior 31 of the cocking seat 30 and ultimately protrudes through an opening 37 in an exterior end 36 of the cocking seat 30.

Looking further to the single use pivot 46, this may be defined by a reduce thickness region in the segment that ultimately defines the engagement element. The pivot 46 may be seen to define a breakable hinge, and is configured such that when the release element 56 engages the engagement element 45, the engagement element 45 pivots on said pivot point and cannot generally return to its pre-pivoted orientation. As a result, even if re-positioning of the engagement element relative to the cocking seat was attempted, the necessary engagement could not be achieved as the reduced thickness portion snaps and or deforms to prevent such re-positioning. A single use of the device is therefore further ensured.

As previously indicated, the cocking seat 30, and preferably the exterior end 36 of the cocking seat 30 may be configured to engage a patient, at least in a general vicinity of a portion to be pierced. Furthermore, in the preferred, illustrated embodiment, the opening 37 at the end 36 of the cocking seat 30 is preferably aligned with a specific location to be pierced, such as on a tip of the finger. That portion of the body, such as the finger, is thereby utilized as an abutment on one of the lancet device 10, while a corresponding support element, such as another finger or a thumb of the patient, or a hand of a medical practitioner or other user, or a solid surface, engages the housing 20 of the lancet device 10. In this regard, as either or both the body section and the support element are moved towards one another such that a spacing therebetween is reduced, the moveable cocking seat 30 moves further into the housing 20 until ultimately the engagement element 45 engages and is released by the released element 56. Once this release is achieved, the lancet 40 moves relative to the cocking seat 30 passing, therethrough such that its piercing tip 42 protrudes from the open end 37 of the cocking seat 30 and piercingly engages the patient's skin. Therefore, in the embodiments of FIGS. 1 and 2 the cocking movement directly results in firing of the lancet 40, requiring only a single, fluid movement to effectively utilize the present lancet device 10. Looking in further detailed to the previous description, it is understood that the effective firing can be achieved either by moving the portion of the patient, such as their finger inward against a fixed support element, by moving a support element towards a fixed portion, of the body to be pierced and/or by compressing both towards one another.

Figure 3:
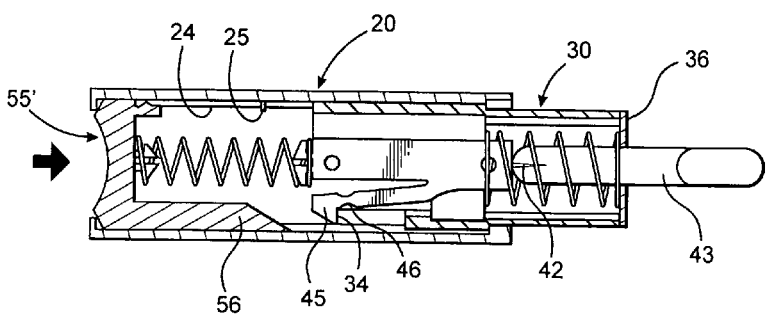
FIG. 3 is a side cross-sectional view of a further embodiment of the lancet device of the present invention.

Turning to the embodiment of FIGS. 3 and 6, it is also understood, that for further safety reasons, if desired, the release element 56 may not necessarily be positioned at all times in an appropriate location to effectively release the lancet 40 from its engagement with the cocking seat 30. For example, in the embodiment of FIG. 3 a stopper 25 is positioned such that movement of the cocking seat 30 and therefore the lancet 40 towards the rear end 55' will not result in a sufficient travel distance such that the engagement element 45 is released by the release element 56. Similarly, in the embodiment of FIG. 6 wherein the cocking seat forms part of the housing and the lancet is re pre-cocked, but does not automatically fire. Rather, in these illustrated embodiments actuation of the rear end 55' inwardly is required so as to effectively move the release element 56 into a position where it may engage the engagement element 45 and provide for appropriate release of the lancet 40 from the cocking seat 30. Also in the embodiment of FIG. 3 a spring or a stopper may be provided so as to also restrict movement of the actuation element 55', as it is ultimately preferred that actuation thereof be utilized only so as to effectively position the release element 56 in a position and orientation such that the previous or subsequent movement of the cocking seat 30 and/or the housing 20 in the manner previously described for cocking and firing results in the releasing engagement between the release element 56 and the engagement element 45. Also on such embodiments it should be recognized that a variety of different actuation assemblies 55' may be effectively provided so as to position the release element 56 in its appropriate position to release the lancet. For example, a side, spring loaded button and/or resilient button may be provided such that the release element 56 is retained at least partially out of the housing and/or out of engaging relation with the engagement element 45 until it is actuated and moved at least partially into the interior of the housing 20. Furthermore, as evidenced by the embodiment of FIG. 6, additional structure may be provided so as to cock the lancet device, or it may be sold pre-cocked with the cocking seat 30 may be pre-positioned in an appropriate position to allow actuation of the release element 56 to effectively disengage the engagement element 45 from the cocking seat 30. As mentioned, in such an embodiment, the cocking seat 30 can be retained in position relative to the housing or can merely be integrally formed with and/or secured to the housing 20, thus eliminating the need to push in the cocking seat 30 and allowing for mere actuation of the release element 56 to result in disengagement of a properly positioned engagement element.

Looking again to FIG. 1, further features that may be provided with the present invention may be the inclusion of cover element 43 which is structured to protect and shield the piercing tip 42 of the lancet 40 prior to use. The cover element 43 preferably extends out from the open interior 31 of the cocking seat 30, out through the opening 37 so as to be effectively grasped by a user for removal thereof when preparing the lancet device 10 for use. Alternately, an exterior cover that covers the cocking seat and/or surrounds the piercing tip may also be provided. It is also noted, that the cocking seat 30 is configured such that even when the cover element 43 is removed, the piercing end 42 is protected and/or shielded within the interior 31 thereof unless and until use. Indeed, it is only when the driving force of the biasing assembly 50 urges the lancet's movement relative to the cocking seat 30 that the piercing tip 42 temporarily passes through the opening 37. Still, as a final safety measure, although a single biasing assembly 50 may be sufficient so as to both drive the lancet 40 into its piercing orientation and so as to generally retracted back into its protective shielding within the cocking seat 30, in some embodiments a secondary biasing assembly 52 may also be positioned and interposed between the lancet 40 and the cocking seat 30, the secondary biasing assembly 52 being structured and disposed so as to not hinder movement of the piercing tip 42 into its piercing orientation, but so as to effectively retract the lancet 40 back into its protective containment within the cocking seat 30. Moreover, that retraction should not be sufficient so as to return the lancet 40 into its engagement relation with the cocking seat 30 for unitary movement therebetween.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A lancet device comprising:
    a housing including an at least partially open interior, a lancet movably disposed within said open interior and including a piercing tip, a biasing assembly disposed within said housing in biasing relation to said lancet and interconnected directly between said housing and said lancet, a cocking seat including an open interior; said cocking seat detached from said lancet and movable in driving relation to said lancet an engagement assembly including an engagement member and a retention member, said engagement member disposed on said lancet and movable both with and relative to said lancet, said retention member mounted on said cocking seat and disposed in continuous driving engagement with said engagement member during a concurrent, forced movement of said lancet and said cocking seat establishing a potential energy of said biasing assembly, said engagement assembly comprising a single use, breakable hinge detachably connecting said engagement member to a remainder of said lancet; said breakable hinge releasably disposing said cocking seat into said continuous driving engagement with said engagement member and said lancet, a release element defined in said housing and disposable into interruptive engagement with said engagement member and deforming, pivoting relation with said breakable hinge upon said concurrent, forced movement of said lancet and said cocking seat establishing a potential energy of said biasing assembly, said breakable hinge including a reduced thickness section structured to break upon said interruptive engagement of said release element with said engagement member and said deforming relation with said breakable hinge, and said biasing assembly biasing said lancet from said open interior of said housing into and through said open interior of said cocking seat upon disengagement between said lancet and said cocking seat.

* * * * *